United States Patent [19]

Marty

[11] Patent Number: 4,814,171

[45] Date of Patent: * Mar. 21, 1989

[54] NOVEL COSMETIC COMPOSITIONS

[75] Inventor: Jean-Pierre Marty, Montesson, France

[73] Assignee: Roussel Uclaf, Paris, France

[*] Notice: The portion of the term of this patent subsequent to Oct. 27, 2004 has been disclaimed.

[21] Appl. No.: 77,426

[22] Filed: Jul. 24, 1987

Related U.S. Application Data

[60] Division of Ser. No. 13,004, Feb. 10, 1987, Pat. No. 4,702,913, which is a continuation-in-part of Ser. No. 686,244, Dec. 26, 1984, abandoned.

[30] Foreign Application Priority Data

Dec. 28, 1983 [FR] France .............................. 83 20926

[51] Int. Cl.$^4$ ............................................. A61K 35/12
[52] U.S. Cl. .................................. 424/95; 424/195.1; 514/725; 514/847; 514/458; 514/80
[58] Field of Search ........................... 514/458; 424/95

[56] References Cited

U.S. PATENT DOCUMENTS 4,551,332  11/1985  Stillman .............................. 514/458

OTHER PUBLICATIONS

Chemie–Chem. Abst., vol. 68 (1968), p. 33,097u.
Williams–Chem. Abst., vol. 83 (1975), p. 26,534r.
Khafizov et al.–Chem. Abst., vol. 91 (1979), p. 73316t.
Fridovich–Ann. Rev. Pharmacol. Toxicol., vol. 23 (1983), pp. 239–257.
Nishikimi et al.–Biochimica et Biophys. Acta, vol. 627 (1980), pp. 101–108.

Primary Examiner—Sam Rosen
Attorney, Agent, or Firm—Bierman & Muserlian

[57] ABSTRACT

Novel cosmetic compositions for skin care and retarding of skin aging effects containing an amount of a mixture of one produce which blocks formation of free radicals and oxygen singlets, oenethera oil and spleen tissue extract sufficient to retard skin aging effects and (e.g. by hydrating and moisturizing the skin) and a method of treating skin.

18 Claims, No Drawings

NOVEL COSMETIC COMPOSITIONS

PRIOR APPLICATION

This application is a division of U.S. patent application Ser. No. 013,004 filed Feb. 10, 1987, now U.S. Pat. No. 4,702,913 a continuation-in-part application of U.S. patent application Ser. No. 686,244 filed Dec. 26, 1984, now abandoned.

STATE OF THE ART

Signs of aging of the skin of people is due to modifications taking place, usually at the epidermal and dermal levels. In the epidermis, the production of new cells no longer compensates for the desquamation and the epidermis gets progressively thinner. The sebaceous glands are functionally less active and therefore the skin becomes dry.

At the level of the dermis, the formation of new collagen which is responsible for the cutaneous tone slows down due to the reduction of the secretion activity of the fibroblasts. Crossed intermolecular liaisons within the collagen fibers multiply, bringing on a structural ridigity, a reduction in the capacity to absorb water, a reduction of nutritional supplies and oxygen. These unfortunate transformations caused a lack of elasticity, dehydration, cutaneous asphyxia and dryness.

These phenomena lead to the appearance of wrinkles, particularly on the face where the skin is particularly attacked by factors of external origin such as bad weather, pollution and luminous radiation and factors of internal origin such as illnesses and increase in age.

Numerous cosmetic preparations intended to combat aging of the skin exist on the market already and these preparations contain very varied compounds such as biological extracts, for example placental extracts, collagen, polyvitamin mixtures, essential fatty acids.

OBJECTS OF THE INVENTION

It is an object of the invention to provide novel skin care compositions which retard the symptoms of skin aging.

It is another object of the invention to provide an improved method of skin care which retards the signs of skin aging.

These and other objects and advantages of the invention will become obvious from the following detailed description.

THE INVENTION

The novel skin care compositions of the invention are comprised of a cosmetic or dermatological composition containing an amount of a mixture of oenothera oil and spleen tissue extract sufficient to retard skin aging effects. Preferably, the compositions contain 2 to 20% by weight of oenothera oil and 2 to 10% by weight of spleen tissue extract.

Oil of oenothera which is very efficient in combatting cutaneous drying for the reasons mentioned above has never been associated with extracts of spleen tissue which are very active against the slowing down of cutaneous cellular activity. Oenothera oil is a substance particularly rich in essential polyunsaturated fatty acids which are nutritional elements indispensable to the organism which it cannot itself synthesize.

The deficiency of essential polyunsaturated fatty acids which increases with age leads to three cutaneous symptoms: namely dry dkin, loss of elasticity and loss of transepidermal water. Oenothera oil, due to its richness in essential fatty acids, linoleic acid, $\gamma$-linolenic acid, arachidonic acid) are indispensable for the integrity of the cellular membranes since they intervene in the role of a barrier applied to the epidermis which controls the loss of water from the skin. The topical application of these 3 essential fatty acis and, particularly $\gamma$-linolenic acid, thus enables the hydration of the skin to be conserved.

The spleen tissue extracts constitute the second essential constituent contained in the cosmetic and dermatological compositions and they contain a mixture of peptides and of proteins obtained especially by proteolysis of bovine spleen. The speen is an organ having a very active metabolism, is rich in cellular base nutrients and particularly in energy-containing intermediates. It has been shown that spleen extracts stimulate the growth and the multiplication of the cells, in particular of the fibroblasts and increase the respiratory cellular activity or increase the consumption of oxygen by fibroblasts. These latter properties prevent the reduction of metabolic cellular activity, a principal cause of the appearance of signs of aging.

Spleen extracts useful in the invention are known and are described in British Pat. No. 1,042,007, for example and have been registered with the FDA under Registration No. CRMCS R 001 4092 on June 23, 1982 and is sold in France under the name Oxydermine.

The spleen tissue extracts are beneficial to the activity of the fibroblast cells of the dermis while oenothera oil, as said above, has beneficial effects for the prevention of epidermal aging and for the improvement of senescent integument. It is therefore useful to associate the two active principles in order to obtain cosmetic or dermatological preparations with synergistic action on the two cutaneous layers, epidermis and dermis, attacked during aging.

For this reason, the association has been carried out and it has been found that the regular application of the compositions of the invention produces a very notable improvement of the hydration and the suppleness of the skin as well as a reduction in wrinkles.

The compositions of the invention can also contain adenosine triphosphate (ATP) as it is or in the form of phosphorylated riboside or salts and cyclic adenosine 3'- 5'- monophosphate (cyclic AMP). The two products increase and/or preserve the energizing potential of the cells of the skin because ATP is the principal energizing element and the cyclic AMP is the intracellular messenger responsible for all the phosphorylations which are indispensable for a certain number of reactions such as the energizing use of glucids (glycogenolysis) and of lipids (lipolysis of the triglycerides).

The compositions such as defined above are characterized in that furthermore they contain adenosine triphosphate (ATP) and in particular in that they contain 0.01 to 5% by weight of adenosine triphosphate. The compositions as defined above may contain cyclic adenosien 3'-5'-monophosphate (cyclic AMP) and in particular 0.01 to 5% by weight of cyclic adenosine 3'-5'-monophosphate.

The compositions can also contain caffeine or theophylline or any product likely to contain them, for examples: tea, coffee. In fact, caffeine and theophylline are methylxanthines and are inhibitors of phsophodiestenase, the enzyme responsibe for the degradation of the cyclic CMP thus allowing the level of cyclic AMP in the compositions to be maintained.

The compositions of the invention may also contain small quantities of solar radiation filters or sun screens, for example, of UVA and UVB radiation filters such as hydroxy 2-methoxy 4-benzophene, and dimethoxy 3,4-phenyl glyoxylic acid in the form of its sodium salt. These compositions can also contain products which block the formation of free radicals and oxygen singlets which enable the solar radiation other than the UV to be blocked. These products are for example, terpenes, liposoluble carrot extract, α-tocopherol.

The compositions may also advantageously contain antioxidants. such as γ-oryzanol. All the substances mentioned above enable the skin to be protected from all harmful solar radiation and a very effective photo-protective action is obtained. The compositions can further contain humectants favoring the hydration of the skin such as urea, pyrrolidone carboxylic acid and its salts, vitamin extracts, perfumes, preservatives, colors.

Collagen, elastin and hyaluronic acid which are substances known as having beneficial properties for the skin can also be present in the compositions of the invention. An extract of horsetail [Equisetum] or any other substance containing silicon which improves the effects of collagen and of the hyaluronic acid can be added.

The cosmetic or dermatological compositions of the invention can be in any form used in cosmetics such as cream or gel in pots or tubes, milk or oil, lotion in a glass or plastic bottle and possibly in a measuring bottle, or in phials. The cosmetic or dermatological compositions may be in the form of a cream, gel, milk, lotion or oil for the skin and in particular, cosmetic or dermatological compositions characterized in that their excipients are adapted for application to the face and the neck.

For each form, the appropriate excipients are used which must have all the usually required qualities. They must be endowed with a great affinity for the skin, be well tolerated, stable, present an adequate consistency enabling easy and pleasant utilization. Examples of excipients are for the cream form a mixture of isopropyl myristate, glycerol stearate, sweet almond oil, cetyl alcohol, polyhydric alcohol (respectively 5 g - 15 g - 6 g - 1 g - 5 g for 100 g of distilled water). The emulsifiers are for example a mixture of methyl glucoside polyoxyethylene (20) sesquistearate and of methyl glucoside sesquistearate.

For the milk form, a mixture of sorbitan monostearate, cetyl polyoxyethyl ether, vaseline oil, isopropyl palmitate, bees-wax, polyhyric alcohol (respectively 1 g - 3 g - 5 g - 5 g - 1 g - 5 g for 100 g of distilled water). For a gel form, an example is carboxyvinylic polymer combined with triethanolamine and an ester of a fatty acid (respectively 3 g - 3 g - 5 g for 100 g of distilled water). For an oil form, triglycerides of fatty acids combined with perhydrosqualene (respectively 30 g and 20 g for 100 g of vegetable oil).

The different cosmetic forms mentioned above can be obtained according to the usual methods used in this field.

In the following examples there are described several preferred embodiments to illustrate the invention. However, it is to be understood that the invention is not intended to be limited to the specific embodiments.

EXAMPLE 1

Cream

| esters of fatty acids | 7 g |
|---|---|
| cetyl alcohol | 1 g |
| glycerol and PEG 100 stearate | 6 g |
| ester of propylene glycol and fatty acids | 7 g |
| benzophenone | 1 g |
| oenothera oil | 5 g |
| glycol propylene | 5 g |
| preservatives | q.s. |
| carboxyvinylic polymer | 0.5 g |
| triethanolamine | 0.5 g |
| extract of spleen tissue (oxydermine) | 3 g |
| aromatic composition | 9 g |
| distilled water q.s. for | 100 g |

EXAMPLE 2

Milk

| glycerol and PEG 100 stearate | 5 g |
|---|---|
| vaseline oil | 3 g |
| silicone oil | 1 g |
| lanolin derivative | 8 g |
| oenothera oil | 3 g |
| sorbitol | 5 g |
| extract of spleen tissue (oxydermine) | 2 g |
| carboxyvinylic polymer | 0.5 g |
| triethanolamine | 0.5 g |
| preservatives | q.s. |
| aromatic composition | q.s. |
| distilled water q.s. for | 100 g |

EXAMPLE 3

Cream

| Lipids of natural and synthetic origin | 15 g |
|---|---|
| oenothera oil | 8 g |
| mixture of mono, di. and trialkylglycolether -o-phosphates | 5 g |
| solar filters UV.A and UV.B | 2 g |
| γ-orizanol | 0.5 g |
| carboxy vinyl polymer | 0.7 g |
| triethanolamine | 0.6 g |
| extracts of spleen tissue (oxydermine) | 3 g |
| extract of coffee/tea | 5 g |
| extract of horsetail [Equisetum] | 1 g |
| ATP disodium salt | 0.02 g |
| urea | 0.5 g |
| Preservatives | q.s. |
| aromatic composition containing terpenes | q.s. |
| Water q.s. for | 100 g |

EXAMPLE 4

Cream

| glucate SS or methyl glucoside sesquistearate | 3 g |
|---|---|
| glucamate SSE 20 or methyl glucoside polyoxyethylene 20 sesquistearate | 2 g |
| oenothera oil | 10 g |
| esters of fatty acids | 7 g |
| sterols of vegetable origin | 5 g |
| liposoluble extract of carrot | 0.2 g |
| γ-tocopherol (vitamin E) | 0.05 g |
| solar filters UV.A and UV.B | 3 g |
| magnesium aluminum silicate | 1.2 g |
| extracts of spleen tissue (oxydermine) | 5 g |
| preservatives | q.s. |
| sodium carboxylate pyrrolidone | 2 g |
| hyaluronic acid | 0.03 g |

-continued

| | |
|---|---|
| ATP phosphoryl riboside | 0.025 g |
| cyclic AMP | 0.02 g |
| aromatic composition | 0.3 g |
| water q.s. for | 100 g |

EXAMPLE 5

The following tests were conducted with cream containing evening primrose oil only (cream C) and a cream containing a mixture of evening primrose oil and spleen extract as claimed in the application (cream A) and a cream containing spleen extract only (cream B) to determine the degree of hydration of the external skin layer, corneum stratum measured with Corneometer CM 420 (Schwartzhaupt).

The creams had the following composition

| | Cream A | Cream B | Cream C |
|---|---|---|---|
| Non-ionic emulsion | 5.5 | 5.5 | 5.5 |
| Esters of fatty acids | 15.0 | 20.0 | 15.0 |
| Fatty alcohol | 1.5 | 1.5 | 1.5 |
| Sun filter | 1.0 | 1.0 | 1.0 |
| Preservative | 0.35 | 0.35 | 0.35 |
| Evening primrose oil | 5.0 | — | 5.0 |
| Polyol | 5.0 | 5.0 | 5.0 |
| Neutralized polymer | 0.5 | 0.5 | 0.5 |
| Spleen extract | 3.0 | 3.0 | — |
| Aromatic composition | 0.4 | 0.4 | 0.4 |
| purified water | qsp 100 | qsp 100 | qsp 100 |

The tests were carried out on six female volunteers with each acting as a control. The application zones were deliminted on the internal face of left and right forearms with zone 1 being in the wrist area, zone 2 being in the middle of the forearm and zone 3 being near the bend of the forearm. Each subject received two applications of a cream containing 5% of evening primrose oil and 3% of spleen extract, two applications of a cream containing 5% only evening prim-rose oil or 3% only spleen extract and two zones served as skin control. The creams were applied uniformly at a dose of 0.1 ml for each deliminted zone of 30 mm and total penetration of the creams was facilitated by a light massage.

The principle of action of the Corneometer CM 420 made possible to detect by the condenser to modify the capacity. The front of the head measured in contact with the modified skin was the capacity according to the degree of hydration of the skin. These modifications are appreciated and directly transcribed by an indicator dial in the form of a number. The results increase with the water contact of the skin and the readings were taken just before the application of the cream and ½; 1, 2, 3 and 4 hours later. For each zone, at different times, averages were taken for 3 tests and then the difference of $T_{30}-T_0$, $T_1-T_0$, $T_2-T_0$, $T_3-T_0$ and $T_4-T_0$ were determined for the two forearms at each time for each subject. The results are shown in the following Table.

TABLE

| | $T_{30}-T_0$ | $T_1-T_0$ | $T_2-T_0$ | $T_3-T_0$ | $T_4-T_0$ |
|---|---|---|---|---|---|
| Cream A containing evening primrose oil + spleen extract | 17.7 | 16.8 | 11.4 | 5.3 | 2.9 |
| Cream B containing spleen extracts only | 15.7 | 16.1 | 8.8 | 1.9 | 1.6 |
| Cream C containing only evening primrose control skin | 8.4 | 6.0 | 5.1 | 3.8 | 2.3 |
| | 2.4 | 2.3 | 2.5 | 1.6 | 0.1 |

CONCLUSION 4 hours after the application of the test creams, the cream of the above application had a clearly superior skin moisturizing power (about twice as great) than the cream containing only evening primrose oil Based on these tests, it can be concluded that the presence of spleen extract clearly reenforces the moisturizing power.

Various modifications of the compositions and method of the invention may be made without departing from the spirit or scope thereof and it is to be understood that the invention is intended to be limited only as defined in the appended claims.

What is claimed is:

1. A skin cosmetic composition for moisturizing skin comprising a cosmetic or dermatological composition containing an amount of a mixture of oenothera oil and spleen tissue extract and at least one product which blocks the formation of free radical and oxygen singlets sufficient to moisturize skin.

2. A composition of claim 1 containing 2 to 20% by weight of oenothera oil and 2 to 10% by weight of spleen tissue extract.

3. A composition of claim 1 also containing adenosine triphosphate.

4. A composition of claim 3 containing 0.01 to 5% by weight of adenosine triphosphate.

5. A composition of claim 1 also containing cyclic adenosine 3',5'-monophosphate.

6. A composition of claim 5 containing 0.01 to 5% by weight of cyclic adenosine 3',5'-monophosphate.

7. A composition of claim 3 also containing cyclic adenosine 3',5'-monophosphate.

8. A composition of claim 4 containing 0.01 to 5% by weight of cyclic adenosine 3',5'-monophosphate.

9. A method of moisturizing skin comprising applying to human skin an amount of a composition of claim 1 sufficient to moisturize the skin.

10. A method of claim 9 containing 2 to 20% by weight of oenothera oil and 2 to 10% be weight of spleen tissue extract.

11. A method of claim 9 also containing adenosine triphosphate.

12. A method of claim 11 containing 0.01 to 5% by weight of adenosine triphosphate.

13. A method of claim 9 also containig cyclic adenosine 3',5'-monophosphate.

14. A method of claim 11 also containing cyclic adenosine 3',5'-monophosphate.

15. A method of claim 13 containing 0.01 to 5% by weight of cyclic adenosine 3',5'-monophosphate.

16. A method of claim 12 containing 0.01 to 5% by weight of cyclic adenosine 3',5'-monophosphate.

17. A composition of claim 1 wherein the product blocking the free radial and oxygen singlet formation is selected from the group consisting of terpenes, liposoluble carrot extract and γ-tocopherol.

18. A method of claim 9 wherein the product blocking the free radial and oxygen singlet formation is selected from the group consisting of terpenes, liposoluble carrot extract and γ-tocopherol.

* * * * *